(12) United States Patent
Kämpf et al.

(10) Patent No.: US 7,538,143 B2
(45) Date of Patent: *May 26, 2009

(54) METHOD FOR THE TREATMENT OF WASTE CONTAINING POLYAMIDE WITH THE REPROCESSING OF THE DEPOLYMERISATION RESIDUE

(75) Inventors: Rudolf Kämpf, Haingründau (DE); Reinhard Wolf, Rodenbach (DE); Joachim Seelig, Biebergemünd (DE)

(73) Assignee: Zimmer Aktiengesellschaft, Frankfurt am Main (DE)

( * ) Notice: Subject to any disclaimer, the term of this patent is extended or adjusted under 35 U.S.C. 154(b) by 290 days.

This patent is subject to a terminal disclaimer.

(21) Appl. No.: 10/897,473

(22) Filed: Jul. 23, 2004

(65) Prior Publication Data

US 2005/0054739 A1 Mar. 10, 2005

(30) Foreign Application Priority Data

Jul. 23, 2003 (DE) ................ 103 33 538

(51) Int. Cl.
*C08J 11/04* (2006.01)
(52) U.S. Cl. .................. 521/40; 540/540; 521/49; 521/49.5; 521/49.8
(58) Field of Classification Search .................. 521/40; 540/540
See application file for complete search history.

(56) References Cited

U.S. PATENT DOCUMENTS

| | | | |
|---|---|---|---|
| 2,752,336 A | 6/1956 | Boon et al. | |
| 2,813,858 A | 11/1957 | Joris | |
| 3,839,324 A | 10/1974 | Schultze et al. | |
| 3,977,952 A | 8/1976 | Knoevenagel et al. | |
| 4,107,160 A | 8/1978 | Dicoi et al. | |
| 4,148,792 A | 4/1979 | Danziger et al. | |
| 4,605,672 A | 8/1986 | Toth et al. | |
| 5,359,062 A | 10/1994 | Fuchs et al. | |
| 5,457,197 A * | 10/1995 | Sifniades et al. | ............ 540/540 |
| 5,598,980 A | 2/1997 | Dilly-Louis et al. | |
| 5,637,700 A | 6/1997 | Fuchs et al. | |
| 5,656,757 A | 8/1997 | Jenczewski et al. | |
| 5,990,306 A | 11/1999 | Mayer et al. | |
| 6,056,633 A | 5/2000 | Sesena et al. | |
| 6,087,494 A * | 7/2000 | Thomissen | ............ 540/540 |
| 6,095,441 A | 8/2000 | Unkelbach et al. | |
| 6,111,099 A * | 8/2000 | Frentzen et al. | ............ 540/540 |
| 6,187,917 B1* | 2/2001 | Mayer et al. | ............ 540/540 |
| 6,579,979 B2 | 6/2003 | Leconte | |
| 7,129,347 B2* | 10/2006 | Kampf et al. | ............ 540/540 |
| 2002/0030014 A1 | 3/2002 | Leconte | |
| 2004/0024204 A1* | 2/2004 | Born et al. | ............ 540/538 |

FOREIGN PATENT DOCUMENTS

| | | |
|---|---|---|
| DE | 887 199 | 8/1953 |
| DE | 889199 | 9/1953 |
| DE | 910 056 | 4/1954 |
| DE | 1105420 | 4/1961 |
| DE | 2408778 | 9/1975 |
| DE | 24 16 573 | 10/1975 |
| DE | 25 07 744 | 9/1976 |
| DE | 19 719 734 | 11/1998 |
| EP | 0 676 394 | 10/1995 |
| EP | 0 681 896 | 11/1995 |
| EP | 0 875 504 | 11/1998 |
| EP | 0 875 505 | 11/1998 |
| EP | 0 876 847 | 11/1998 |
| IN | 142150 | 6/1977 |
| JP | 5313636 | 11/1993 |
| JP | 8099954 | 4/1996 |
| JP | 2000038377 | 2/2000 |

OTHER PUBLICATIONS

Brandup, et al., "Die Wiederverwertung von Kunststoffen", (The Recycling of Plastics), Verlag Carl Hanser Munich, Vienna, 1995, pp. 513-520. (English Translation).
Organikum, Organisch-chemisches Grundpraktikum, Veb Deutscher Verlag der Wissenschaften, Berlin 1988, pp. 54-59.

* cited by examiner

*Primary Examiner*—Katarzyna Wyrozebski
(74) *Attorney, Agent, or Firm*—Michael Best & Friedrich LLP

(57) ABSTRACT

The invention relates to a method for the treatment of waste containing polyamide comprising a) depolymerisation of the waste containing polyamide, whereby a caprolactam raw material (6) and a flow (3), comprising the secondary constituents and additives from the depolymerisation, are obtained, and b) leaching of the flow (3) at least once using an extracting agent.

23 Claims, 1 Drawing Sheet

Figure 1:
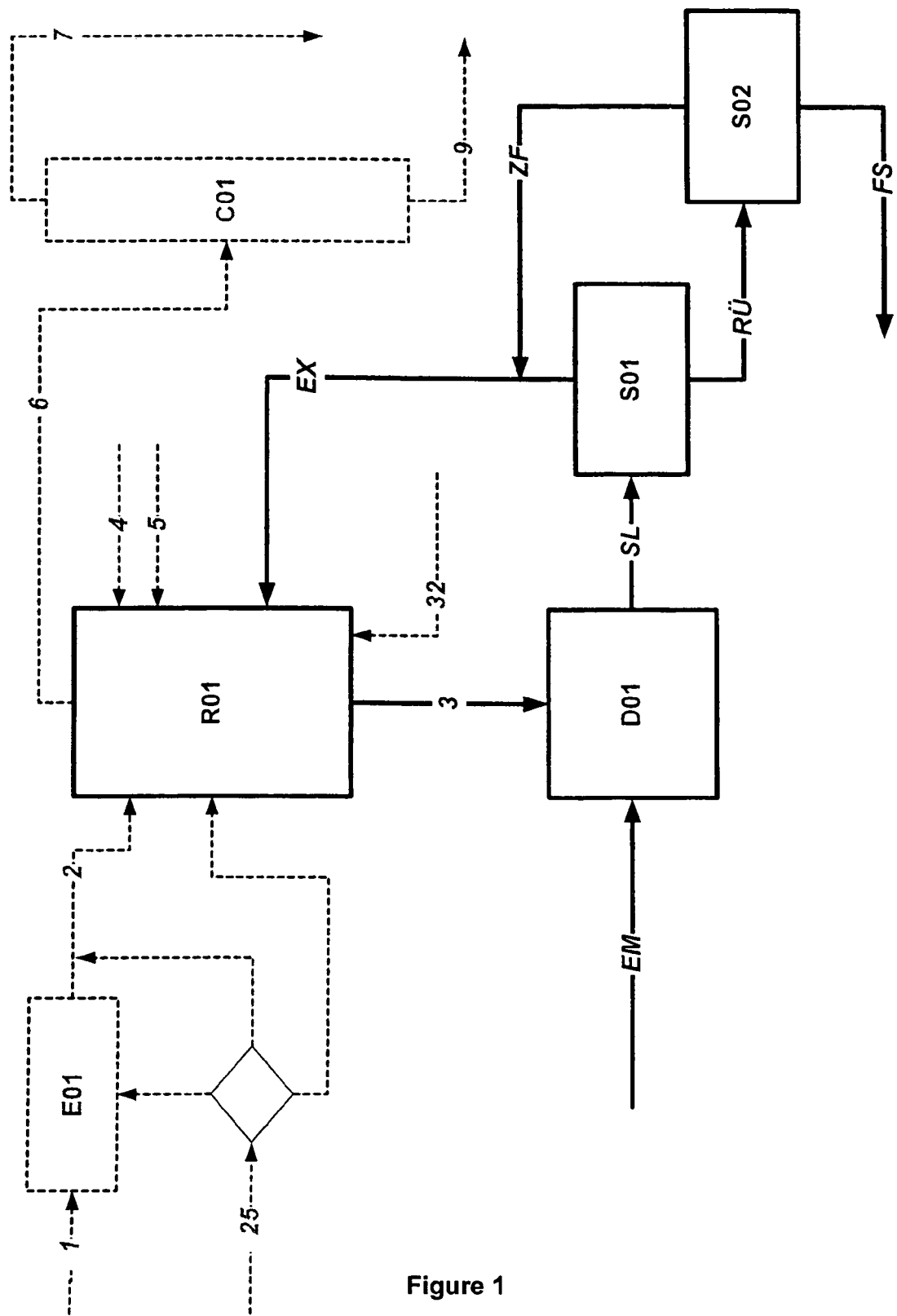

METHOD FOR THE TREATMENT OF WASTE CONTAINING POLYAMIDE WITH THE REPROCESSING OF THE DEPOLYMERISATION RESIDUE

RELATED APPLICATIONS

This application claims the foreign priority under 35 USC §119 of German Patent No. 10333538.2 filed on Jul. 23, 2003.

This invention relates to a continuous method for the treatment of waste containing polyamide including improvement of the economic efficiency by feeding back valuable substances from the cracking reactor discharge during the reprocessing of polyamide 6 from polyamide waste by acid catalysed cracking to highly pure caprolactam suitable for polycondensation.

Reprocessing by the cracking of clean, unprocessed, brand-new polyamide waste directly resulting from production to products with quality features as exhibited by new goods is possible without any special measures. If consumer articles have been used for many years or products from a collection of plastics are to be used, this can only be carried out with increased costs in terms of technology and energy. Cleaning and sorting stages are necessary in this case as described, for example, in DE 197 19 734, EP 0 681 896, U.S. Pat. No. 5,598,980, DE 2416 573, DE 25 07 744, in order to obtain a polyamide 6 fraction of a pure grade. These process steps are essential, because plastic products are always adapted to the respective field of application. For this reason they contain manufacturer-specific and production-specific additives, dyes, stabilisers, glass fibres, etc. which impair reprocessing without additional measures. With the reprocessing of polyamide waste and recycling into the material circulation the breakdown into monomers is inevitable if a product is to be produced which is not different from goods produced out of monomers from the synthesis route.

One of the most important process steps, as can be taken from DE 887199, EP 0 875 505, DE 910056, U.S. Pat. No. 4,605,672, JP 53-13636 and the relevant (German) literature, for example, Brandrup/Bittner/Michaeli/Menges "Die Wiederverwertung von Kunststoffen" ("The reprocessing of plastics"), pp. 513-520, Verlag Carl Hanser Munich Vienna 1995, is the alkali or acid catalysed cracking and decanting of caprolactam using water-vapour distillation. Since polyamide 6 products as mentioned above is not usually the only material fed into a cracking reactor, interfering or additive substances must be expelled continually or at time intervals. The interfering and additive substances with the reprocessing of polyamide 6 carpets arise in that the fibres designated as the pile or also the wear layer are needled onto a substrate, e.g. polypropylene fibrous web, during the manufacture of the carpet. After the application of the pile, fixing follows using an adhesive layer, onto which a polymer foam backing, filled with a filler substance such as chalk, is applied. During reprocessing, the pile or the wear layer is separated from pulverised carpet material and is passed to a depolymerisation process for recovery of the monomers. In the depolymerisation, cracking of the polymer chains occurs, for example, according to the methods known from DE 887 199, EP 0 875 504, DE 910056, U.S. Pat. No. 4,605,762, JP 53-13636 using phosphoric acid and introduced steam drives off the resulting caprolactam as a water vapour mixture.

The mechanical processing and separation according to the sink-and-float centrifuge technology, as carried out for example in carpet processing plants in the USA or in Germany, does not fully separate pure pile or wear layer in polyamide 6. Interference materials, such as proportions of SBR foam backing, chalk from the processing, soot, web residues and other filler materials do remain. In the course of the commercial operation of a carpet processing plant it has been found to be advantageous in the core section, namely the caprolactam recovery system, to expel as residue these secondary constituents, controlled by analyses and on-line measurements of the phosphoric acid content. The monitoring and control of the expelled mass through analyses and on-line measurements of the phosphoric acid content in the flow has proved to be especially advantageous with regard to the economic operation of such a plant, because as a result it was possible to minimise the consumption of phosphoric acid on one hand and the consumption of alkali for neutralisation of the residue on the other. Furthermore, due to the measurement and monitoring of the nitrogen content in the expelled material flow, the polymer chain cracking and therefore the yield of caprolactam compared to a method of operation without nitrogen monitoring were able to be increased advantageously.

A disadvantage of the method described above is the fact that the expelled residue is neutralised with substantial amounts of alkali in order to bind the expelled and unused phosphoric acid.

It is therefore the object of this invention to provide a more economically efficient method for the processing of the expelled residue.

The solution of the object is a method for the treatment of waste containing polyamide, comprising
  a) depolymerisation of the waste containing polyamide, whereby a caprolactam raw material (6) and a flow (3) are obtained, which comprises secondary constituents and additives of the depolymerisation, and
  b) leaching of the flow (3) at least once using an extracting agent.

The waste containing polyamide which is used in the method according to the invention is preferably selected from used, contaminated polyamide 6 waste or polyamide 6 waste taken from the recycling system. The waste containing polyamide is particularly preferably selected from the group consisting of moulded parts containing polyamide, such as parts for vehicles, injection moulded parts with glass fibres and other additives containing polyamide and fibres, carpets, carpet floor coverings and other objects from daily life containing polyamide, such as clothing. The material containing polyamide which is fed into the depolymerisation may also contain non-polymers and other types of additives.

The waste containing polyamide can be preferably melted before carrying out the depolymerisation in stage a). In addition, other products can be added to it which originate from a caprolactam distillation.

The depolymerisation in stage a) of the method according to the invention is carried out according to known methods, such as acid cracking, for example using phosphoric acid, alkali cracking or vapour cracking. Preferably, the depolymerisation is carried out in stage a) using phosphoric acid. The caprolactam raw material obtained after the depolymerisation can be concentrated and passed on for further required applications, such as the manufacture of polyamide. The further flow obtained after depolymerisation comprises the residues of the respective crackings, namely including secondary constituents and additives. The secondary constituents contained in the flow (3) are valuable constituents which can be used further, such as cracking acids or alkalies, cracking products from the polyamide cracking and 6-amino caproic acid, caprolactam and cyclical and linear polyamide oligomers. If acid cracking is carried out using phosphoric acid, the secondary constituents comprise phosphoric acid, caprolactam, cracking products of the polyamide cracking, cyclical and linear polyamide oligomers and 6-amino caproic acid.

The additives, which are also contained in the flow (3), cannot be used further and comprise, for example, glass fibres, chalk, barite, soot, kaolin, bentonite, silicates and dyes.

The flow (3) is then leached in stage b) of the method according to the invention. "Leaching" in the sense of this invention signifies bringing the flow (3) into contact with an extracting agent.

The leaching takes place preferably with a single or a mixture of several extracting agents selected from the group consisting of water, alcohols, alkyl carbonates, amines and their aqueous mixtures. Pure water is used particularly preferably. But also for example 10-80% by mass of aqueous mixtures of methanol, ethanol, isopropanol or ethylene carbonate can be used to advantage. The low alcohols are themselves in contrast less suitable due to their low boiling points and the light flammability of their vapours.

To obtain the required contact time between the flow (3), which contains the solids, namely secondary constituents and additives or is composed of such solids, and the extracting agent, a slurry is made of the flow (3) containing the solids and the extracting agent.

If the method according to the invention in stage a) is carried out using phosphoric acid, the contents of flow (3) include, among others, 6-amino caproic acid, caprolactam and phosphoric acid, which are three valuably raw materials. By carrying out stage b) of the method according to the invention the amino caproic acid dissolves, as does the cracking product caprolactam and the cracking acid, such as phosphoric acid, very well in the extracting agent, such as water, alcohols, alkyl carbonates or their mixtures, whereby however the solubility in water is higher than in mixtures of alcohols or amines. Therefore it is preferable to use water as the extracting agent.

For example, 800 g/l of amino caproic acid and 4560 g/l of caprolactam dissolve in water at 20° C. The good solubility results in the solutions becoming saturated and for extraction at high temperatures only slight quantities of water are needed.

Advantageously, approximately 150 to approximately 5000 g of extracting agent, in particular water, can be used per 100 g of flow (3) in stage b).

It is preferable to carry out stage b) at elevated temperatures, in particular from room temperature to about 5 to about 10° C. below the boiling point of the extracting agent, preferably from about 30° C. to about 5° C. below the boiling point of the extracting agent. If water is used as the extracting agent, stage b) is preferably carried out at about 40° C. to 95° C. If extracting agents, such as low alcohols, amines or alkyl carbonates are used, then their boiling points are usually lower than that of water. In order to maintain a certain margin to the boiling point, the highest temperature during extraction should be at least 5 to 10° C. below the boiling point. Advantageously, cyclical carbonates are used as the extracting agent, because they have higher boiling points than water and similarly high dissolving and supersaturation properties as water and can therefore be used up to temperatures of 220° C.

Furthermore, it is preferable if the flow (3) includes solids with a grain size of up to 5 mm and especially up to 2 mm.

Preferably stage b) of the method according to the invention is carried out over a period of about 5 minutes to about 4 hours.

After leaching in stage b) of the method, a mixture is then obtained, in which the solid, which contains the additives and, where applicable, other secondary constituents, and an extracting agent with the secondary constituents dissolved in it, such as 6-amino caproic acid, phosphoric acid and other valuable polyamide cracking products, are contained. This mixture is especially a slurry. Preferably, this mixture is then separated into a liquid part and a part containing the solids. The method according to the invention therefore includes a further stage c), namely the separation of the solids from the extracting agent with the secondary constituents dissolved in it.

The separation of the mixture obtained after stage b), in particular a slurry, in stage c) of the method can occur preferably by mechanical separation, such as by letting the mixture stand, in particular the slurry, whereby the solids drop down, and with separation of the liquid excess or by centrifuging. Preferably stage c) is carried out in a solids separator.

Advantageously, the separated liquid part, namely the extracting agent with the secondary constituents dissolved in it, can then after stage c) be fed back into stage a).

In addition the part containing the solids obtained after stage c) can in turn be fed back into stage b) of the method, i.e. passed to another leaching of the solids with extracting agent, whereby this solid corresponds to the flow (3) during the first pass through the method. The part obtained after carrying out stage c) and containing the solids can also be leached together with the flow (3) in stage b) of the method according to the invention. Also after the second pass of the stage b) an extracting agent containing secondary constituents and a part containing solids is obtained, whereby this mixture is in turn preferably separated into a liquid part and a part containing the solids. The liquid part containing the secondary constituents can in turn be fed back again to stage a).

As can be seen from the above, stages b) and c) of the method according to the invention can be carried out many times, preferably up to five times, whereby in each case the liquid part obtained after stage c) and containing the valuable secondary constituents can be fed back to stage a) and the part containing the solids obtained after stage c) is fed back again to stage b).

The liquid part obtained after carrying out stage c), which contains the extracting agent and secondary constituents, preferably has a concentration of up to 90% of the saturation limit of the respective constituents in the extracting agent used.

The part containing solids obtained after carrying out stage c) can, if its content of valuable secondary constituents is low, be expelled from the circulatory loop after leaching.

The method according to the invention enables a recovery of up to 80% of the remaining secondary constituents of the depolymerisation, namely the valuable substances in the expelled residue. In particular, by carrying out the method according to the invention more than 80% by mass of amino caproic acid, more than 70% of other polyamide cracking products, such as for example caprolactam and unreacted phosphoric acid, can be extracted from the flow (3).

Through the method according to the invention an improvement in the economic efficiency of a polyamide depolymerisation plant is obtained in that the expelled residue from the depolymerisation is released by the leaching of soluble constituents at least once and consequently its valuable constituents become available for further use. The processing of the expelled residue from the depolymerisation reactor has therefore had an advantageous economic effect on the reprocessing and is characterised in that valuable substances such as phosphoric acid, 6-amino caproic acid and other soluble valuable substances are recovered through extractive leaching of the residue. Returning an extract of the residue from the depolymerisation reactor with the phosphoric acid and 6-amino caproic acid it essentially contains, on one hand advantageously reduces the acid consumption by 3 to 5% and on the other hand surprisingly increases the content of caprolactam in the vapours, i.e. the caprolactam raw material, from the depolymerisation reactor. The return of 6-amino caproic acid to the point of the reactor activity or its generation has surprisingly proven to be particularly advantageous, because during a verification through specific charging of only 6-amino caproic acid in a concentration and quantity corresponding to the expulsion, this measure has led to an increase in the yield of caprolactam in the stripped vapours of the depolymerisation reactor by at least 3 to 5% by mass. This increase presumably forms a thermodynamic/reaction equilibrium with caprolactam and is formed as a consequence of the hydrolysis out of the ring-shaped lactam by the inclusion of a water molecule.

Valuable substances such as phosphoric acid, 6-amino caproic acid and other soluble valuable substances are recovered and returned to the depolymerisation reactor as an extract of the residue from the depolymerisation reactor. The return feeding of 6-amino caproic acid to the depolymerisation reactor leads to an increase in the caprolactam yield.

FIG. 1 shows a system which is suitable for carrying out the method according to the invention.

Equipment
E01 Melting equipment
C01 Concentrating device
D01 Extraction apparatus
R01 Depolymerisation reactor
S01 First solids separator
S02 Second solids separator Material flows
1 Polyamide 6 waste
2 Melt
3 Expulsion, depolymerisation
4 Vapour, polyamide extraction/concentration
5 Phosphoric acid
6 Raw lactam/water
7 Steam
8 Raw lactam concentrate
25 Raw caprolactam residue
32 Polyamide extract concentrate from the product granulate extraction
EM Extracting agent
EX Extract
FS Solids expulsion
RÜ Separation residue
SL Suspension residue, extracting agent
ZF Centrifugate The method according to the invention for increasing the economic efficiency of the treatment of polyamide waste will now be explained in more detail based on FIG. 1.

Polyamide 6 waste recovered by mechanical methods is fed, as shown in FIG. 1, via the feed line 1 to a melting extruder E01 with other products from a caprolactam distillation. The polymer melt leaving the melting apparatus E01 is continually fed via the feed line 2 to the depolymerisation reactor R01 in which, following known methods according to DE 887199, EP 0 875 504, DE 910056, U.S. Pat. No. 4,605,762 and JP 53-13636, cracking of the polymer chains occurs by means of phosphoric acid 5. Here, caprolactam forms, which is driven off by introducing steam 4 by means of the head 6 and fed to a concentrating device C01.

Since the mechanical processing and separation according to the sink-and-float centrifuge technology does not supply the extruder E01 with polymer completely free of interfering substances, in which proportions of SBR foam backing and chalk from the processing of carpets, soot, web residues and other filler materials are contained in the material flow 2, a residue remains in the depolymerisation reactor R01, which must be expelled continuously or at time intervals. Although it has been proven to be favourable during the commercial operation of a caprolactam recovery plant to expel these secondary constituents continuously via the residue line 3, controlled by on-line analyses and measurements of the phosphoric acid content, these measures were not able to prevent losses of valuable material occurring. Additional costs arise due to the addition of alkaline solution in order to render the acidic residue 3 disposable.

For the operation of the depolymerisation system an improvement in the economic efficiency has been proven when valuable, unreacted phosphoric acid and the 6-amino caproic acid occurring as a secondary product during the polyamide cracking are recovered by leaching of the solids in an extraction apparatus D01. The slurry SL leaving the extraction apparatus D01 is passed to a solids separator S01 and the liquid EX standing over the residue is returned to the depolymerisation reactor. The solid RÜ coming from the bottom of the first separator S01 enters the second solids separator S02, in which for example extensive removal of the liquid content occurs by centrifuging. Also this liquid flow designated as centrifugate ZF is returned to the depolymerisation reactor R01 combined with the extract EX from stage 1. The leached and almost dry solid FS can be disposed of with sewage sludge.

The invention is explained in further detail based on an example.

EXAMPLE

A residue flow is continuously drawn off through a bottom drain valve and a discharge pump from a cracking reactor of a carpet recycling plant for the recovery of caprolactam from sorted nylon 6 floor coverings. This flow is adjusted such that the residue concentration in the cracking reactor remains constant. The volume flow varies in a range for sludge removal from concentration systems known to the specialist and is 3 to 5% by mass of the fed flow 2. The residue flow 3 is composed primarily of mixed salts of alkali and earthy base carbonates and phosphates, unreacted polyamides and amino caproic acid. Amino caproic acid is present as a hydratized form of the cyclical caprolactam in equilibrium with it and is continually reformed to maintain the equilibrium, so that it is removed from the process.

The melt 3 discharged from the cracking reactor R01 exhibits a temperature of between 150° C. to 300° C. depending on the operating mode of the reactor and still contains, depending on the operating mode, 3 to 12% by mass of amino caproic acid and other polyamide cracking products. The molten reactor discharge 3 is fed to the extraction apparatus D01 in which soluble parts are dissolved from the product even during the quenching phase.

By bringing the hot melt into the extracting agent, for example water, apart from giving a fine distribution, the heating of the water or extracting agent, which, due to the suitable charging of fresh or recycled water or extracting agent EM, can be increased to boiling point. It is advantageous to work with water at temperatures up to 90° C., because here an operationally economical optimum is obtained between vaporising quantities of water and the saturation concentration of amino caproic acid. Due to a tumbler device the finely distributed solid is brought into contact with the extracting agent with a mean dwell time of 5 minutes to 4 hours, advantageously 1.5 hours, whereby more than 80% by mass of amino caproic acid, polyamide cracking products and unreacted cracking acid, for example phosphoric acid, is dissolved from the inorganic matrix. The solution containing solids is transported using pumps to the following separation stages for separation of the solid from the solution. In the first solids separator S01, which consists of a conical sedimentation container, the solid particles can settle out with a mean dwell period from 5 minutes to 12 hours at temperatures between 15° C. and 90° C. The remaining solution EX containing between 5 and 75% by mass of amino caproic acid, polyamide cracking products and cracking acid is returned using pumps to the cracking reactor R01.

The solid constituents RÜ situated on the bottom are transported from there by means of a feed screw into the second solids separator S02 to recover the clinging solution. This second solids separator consists of a continuously operated decanter, with the aid of which the solution clinging to the solids is almost completely extracted.

In addition, the decanter exhibits a flushing device, with the aid of which the solid can be washed with pure extracting agent.

The solid flow FS leaving the decanter exhibits only a low moisture content of less than 10% by mass and is suitable without further drying, for example due to its high earthy base and phosphor content, as a fertiliser.

The separated liquid ZF is combined with the extract flow EX from the first solids separation and returned together to the cracking reactor R01.

The invention claimed is:

1. Method for the treatment of waste containing polyamide, comprising
   a) depolymerisation of the waste containing polyamide in a depolymerization reactor, whereby a caprolactam raw material and a flow, comprising secondary constituents and additives from the depolymerisation, are obtained, the flow leaving the reactor separately from the caprolactam raw material, and
   b) leaching of the flow separated in step (a) at east once using an extracting agent to form a slurry, wherein one or more of the secondary constituents selected from the group consisting of a cracking acid, a cracking alkali, 6-amino caproic acid, a cyclical polyamide oligomer and a linear polyamide oligomers is dissolved in the extracting agent, and wherein the extracting agent comprises at least one of water, an alcohol, an alkyl carbonate, or an amine.

2. Method according to claim 1, whereby the waste containing polyamide is selected from the group consisting of moulded parts containing polyamide, injection moulded parts with glass fibres containing polyamide and other additives and fibres, carpets, carpet floor coverings containing polyamide and other objects containing polyamide from daily life.

3. Method according to claim 1, whereby the depolymerisation is carried out in stage a) through acidic, alkali, and/or vapour-cracking.

4. Method according to claim 3, whereby the acidic cracking is carried out using phosphoric acid.

5. Method according to claim 4, whereby the flow comprises as secondary constituents phosphoric acid, caprolactam, other polyamide cracking products and 6-amino caproic acid.

6. Method according to claim 1, whereby the leaching is carried out in stage b) and wherein the extracting agent is water.

7. Method according to claim 1, additionally comprising stage c) with separation at least once of a mixture obtained after stage b) into a liquid part and a) part containing solids.

8. Method according to claim 7, whereby the liquid part obtained after stage c) is returned to stage a).

9. Method according to claim 7, whereby the obtained part containing solids in stage b) is either returned completely or as a partial flow of the process.

10. Method according to claim 8, whereby the obtained part containing solids in stage b) is either returned completely or as a partial flow of the process.

11. Method according to claim 7, wherein the separation of stage c) occurs by settling or centrifugation.

12. Method according to claim 7, wherein the separation of stage c) is carried out in a solids separator.

13. Method for the treatment of waste containing polyamide, comprising
   a) depolymerisation of the waste containing polyamide, whereby a caprolactam raw material and a flow, comprising secondary constituents and additives from the depolymerisation, are obtained, and
   b) contacting the flow with an extracting agent to form a slurry, and leaching the flow at about 30° C. to about 5° C. below the boiling point of the extracting agent, wherein one or more of the secondary constituents selected from the group consisting of a cracking acid, a cracking alkali, 6-amino caproic acid, a cyclical polyamide oligomer and a linear polyamide oligomer is dissolved in the extracting agent, and wherein the extracting agent comprises at least one of water, an alcohol, an alkyl carbonate, or an amine.

14. Method according to claim 13, further comprising
   c) separation of the slurry of stage b) into a liquid part and a part containing solids.

15. Method according to claim 14, wherein the separation of stage c) occurs by settling or centrifugation.

16. Method according to claim 14, wherein the separation of stage c) is carried out in a solids separator.

17. Method for the treatment of waste containing polyamide, comprising
   a) depolymerisation of the waste containing polyamide, whereby a caprolactam raw material and a flow, comprising secondary constituents and additives from the depolymerisation, are obtained, and
   b) contacting the flow with an extracting agent comprising water to form a slurry, and leaching the flow at about 40° C. to about 95° C., wherein one or more of the secondary constituents selected from the group consisting of a cracking acid, a cracking alkali, 6-amino caproic acid, a cyclical polyamide oligomer and a linear polyamide oligomer is dissolved in the extracting agent, and wherein the extracting agent comprises at least one of water, an alcohol, an alkyl carbonate, or an amine.

18. Method according to claim 17, further comprising
   c) separation of the slurry of stage b) into a liquid part and a part containing solids.

19. Method according to claim 18, wherein the separation of stage c) occurs by settling or centrifugation.

20. Method according to claim 18, wherein the separation of stage c) is carried out in a solids separator.

21. Method according to claim 1, wherein the secondary constituents dissolved in the extracting agent in step (b) further comprise caprolactam residue.

22. Method according to claim 13, wherein the secondary constituents dissolved in the extracting agent in step (b) further comprise caprolactam residue.

23. Method according to claim 17, wherein the secondary constituents dissolved in the extracting agent in step (b) further comprise caprolactam residue.

* * * * *